United States Patent
Eddy

(10) Patent No.: US 11,998,650 B2
(45) Date of Patent: *Jun. 4, 2024

(54) METHOD OF LIMITING THE SPREAD OF NOROVIRUS WITHIN A CRUISE SHIP

(71) Applicant: Parasol Medical, LLC, Buffalo Grove, IL (US)

(72) Inventor: Patrick E. Eddy, Allendale, MI (US)

(73) Assignee: Parasol Medical, LLC, Buffalo Grove, IL (US)

(*) Notice: Subject to any disclaimer, the term of this patent is extended or adjusted under 35 U.S.C. 154(b) by 643 days.

This patent is subject to a terminal disclaimer.

(21) Appl. No.: 17/141,756

(22) Filed: Jan. 5, 2021

(65) Prior Publication Data

US 2021/0121591 A1    Apr. 29, 2021

Related U.S. Application Data

(63) Continuation of application No. 15/807,157, filed on Nov. 8, 2017, now Pat. No. 10,967,082.

(51) Int. Cl.
*A61L 2/18* (2006.01)
*A01N 25/02* (2006.01)
*A01N 55/00* (2006.01)

(52) U.S. Cl.
CPC ............... *A61L 2/18* (2013.01); *A01N 25/02* (2013.01); *A01N 55/00* (2013.01); *A61L 2202/25* (2013.01)

(58) Field of Classification Search
CPC .......... A61L 2/18; A61L 2202/25; A61L 2/22; A61L 2101/12; A61L 2101/18; A01N 25/02; A01N 55/00; G06Q 50/30
See application file for complete search history.

(56) References Cited

U.S. PATENT DOCUMENTS

| 3,241,152 A | 3/1966 | Hay |
| 3,515,131 A | 6/1970 | Stevens |

(Continued)

FOREIGN PATENT DOCUMENTS

| EP | 0108853 A1 | 5/1984 |
| EP | 0129980 A2 | 1/1985 |

(Continued)

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

(Continued)

*Primary Examiner* — Regina M Yoo
(74) *Attorney, Agent, or Firm* — Price Heneveld LLP

(57) ABSTRACT

A method of limiting the spread of the norovirus within a cruise ship comprising: identifying a surface within a common area of a cruise ship that passengers are likely to touch; and applying a silane quaternary ammonium ion or salt thereof to the surface. The common area can be an elevator and the surface an elevator button. The common area can be a stairway and the surface a handrail. The common area can be a casino. The common area can be a dining room. The common area can be a walkway and the surface a handrail. The silane quaternary ammonium ion or salt thereof can be 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. Applying the silane quaternary ammonium ion or salt thereof to the surface comprises applying a solution including the silane quaternary ammonium ion or salt thereof and a solvent.

18 Claims, 8 Drawing Sheets

(56) References Cited

U.S. PATENT DOCUMENTS

| | | |
|---|---|---|
| 3,654,165 A | 4/1972 | Bryant et al. |
| 4,017,662 A | 4/1977 | Gehman et al. |
| 4,266,669 A | 5/1981 | Watson |
| 4,282,366 A * | 8/1981 | Eudy .................... C07F 7/1804 106/18.32 |
| 4,372,303 A | 2/1983 | Grossmann et al. |
| 4,394,378 A | 7/1983 | Klein |
| 4,414,268 A | 11/1983 | Baldwin |
| 4,504,541 A | 3/1985 | Yasuda et al. |
| 4,603,152 A | 7/1986 | Laurin et al. |
| 4,735,198 A | 4/1988 | Sawa |
| 4,797,420 A | 1/1989 | Bryant |
| 4,865,844 A | 9/1989 | Blank et al. |
| 4,891,846 A | 1/1990 | Sager et al. |
| 4,921,691 A | 5/1990 | Stockel |
| 5,003,970 A | 4/1991 | Parker et al. |
| 5,079,004 A | 1/1992 | Blank et al. |
| 5,183,664 A | 2/1993 | Ansell |
| 5,193,549 A | 3/1993 | Bellin et al. |
| 5,270,358 A | 12/1993 | Asmus |
| 5,277,698 A | 1/1994 | Taylor |
| 5,411,585 A | 5/1995 | Avery et al. |
| 5,428,078 A | 6/1995 | Cohen et al. |
| 5,466,898 A | 11/1995 | Gilbert et al. |
| 5,520,664 A | 5/1996 | Bricault, Jr. et al. |
| 5,592,946 A | 1/1997 | Eddy |
| 5,620,001 A | 4/1997 | Byrd et al. |
| 5,660,182 A | 8/1997 | Kuroshaki et al. |
| 5,685,866 A | 11/1997 | Lopez |
| 5,762,623 A | 6/1998 | Murphy et al. |
| 5,954,869 A | 9/1999 | Elfersy et al. |
| 5,959,014 A | 9/1999 | Liebeskind et al. |
| 6,186,957 B1 | 2/2001 | Milam |
| 6,221,944 B1 | 4/2001 | Liebeskind et al. |
| 6,224,579 B1 | 5/2001 | Modak et al. |
| 6,344,025 B1 | 2/2002 | Inagaki et al. |
| 6,420,455 B1 | 7/2002 | Landgrebe et al. |
| 6,492,012 B1 | 12/2002 | Shah |
| 6,495,229 B1 | 12/2002 | Carte et al. |
| 6,520,281 B1 | 2/2003 | Deslauriers et al. |
| 6,575,917 B2 | 6/2003 | Giroux et al. |
| 6,738,986 B1 | 5/2004 | Martin |
| 6,803,034 B2 | 10/2004 | DuVal et al. |
| 6,821,936 B2 | 11/2004 | Green et al. |
| 6,821,943 B2 | 11/2004 | Avery et al. |
| 6,822,030 B2 | 11/2004 | Olson et al. |
| 6,994,890 B2 | 2/2006 | Ohlhausen et al. |
| 7,045,673 B1 | 5/2006 | Batich et al. |
| 7,081,101 B1 | 7/2006 | Sawa |
| 7,201,914 B2 | 4/2007 | Dees |
| 7,645,824 B2 | 1/2010 | Hendriks et al. |
| 7,674,473 B2 | 3/2010 | Falder et al. |
| 7,704,313 B2 | 4/2010 | Ohlhausen et al. |
| 7,709,694 B2 | 5/2010 | Batich et al. |
| 7,731,564 B2 | 6/2010 | Sanders |
| 7,754,004 B2 | 7/2010 | Ohlhausen et al. |
| 7,754,625 B2 | 7/2010 | Hendriks et al. |
| 7,790,217 B2 | 9/2010 | Toreki et al. |
| 8,025,120 B2 | 9/2011 | Eddy |
| 8,178,484 B2 | 5/2012 | Schwarz et al. |
| 8,257,780 B2 | 9/2012 | Ohlhausen et al. |
| 8,440,217 B1 | 5/2013 | El-Naggar et al. |
| 8,449,483 B2 | 5/2013 | Eddy |
| 8,491,922 B2 | 7/2013 | Eddy |
| 8,574,844 B2 | 11/2013 | Burkhardt, III et al. |
| 8,639,527 B2 | 1/2014 | Rensvold et al. |
| 8,679,526 B2 | 3/2014 | Van Den Plas et al. |
| 8,916,742 B2 | 12/2014 | Smith |
| 8,956,665 B2 | 2/2015 | Bolkan et al. |
| 8,999,363 B2 | 4/2015 | Elfersy |
| 9,028,846 B2 | 5/2015 | Eddy |
| 9,089,138 B2 | 7/2015 | Higgins et al. |
| 9,095,731 B2 | 8/2015 | Gentle et al. |
| 9,149,393 B2 | 10/2015 | Cumming et al. |
| 9,204,677 B2 | 12/2015 | Abbey et al. |
| 9,215,903 B2 | 12/2015 | Abbey et al. |
| 9,254,591 B2 | 2/2016 | Fox et al. |
| 9,375,346 B1 | 6/2016 | Sundheimer et al. |
| 9,433,708 B2 | 9/2016 | Eddy |
| 9,675,735 B2 | 6/2017 | Eddy |
| 9,717,249 B2 | 8/2017 | Eddy |
| 9,757,769 B2 | 9/2017 | Grossman et al. |
| 9,795,141 B2 | 10/2017 | Chason et al. |
| 9,795,177 B1 | 10/2017 | Weaver |
| 9,834,874 B2 | 12/2017 | Stein |
| 9,840,626 B2 | 12/2017 | Farrugia et al. |
| 9,845,569 B2 | 12/2017 | Dunn et al. |
| 9,855,584 B2 | 1/2018 | Grossman et al. |
| 9,877,875 B2 | 1/2018 | Eddy |
| 9,877,879 B2 | 1/2018 | Beck |
| 9,943,135 B2 | 4/2018 | Baychar |
| 10,039,683 B2 | 8/2018 | Jung et al. |
| 10,045,536 B2 | 8/2018 | Chason et al. |
| 10,212,932 B2 | 2/2019 | Chiattello et al. |
| 10,258,046 B2 | 4/2019 | Grossman et al. |
| 10,258,411 B1 | 4/2019 | Ferguson |
| 10,306,884 B1 * | 6/2019 | Howard, Jr. ........... A01N 25/02 |
| 10,388,143 B2 | 8/2019 | Eddy et al. |
| 10,470,689 B2 | 11/2019 | Kilcran et al. |
| 10,472,157 B1 | 11/2019 | Dudding et al. |
| 10,758,426 B2 | 9/2020 | Eddy |
| 10,822,502 B2 | 11/2020 | Eddy |
| 10,864,058 B2 | 12/2020 | Eddy |
| 10,967,082 B2 | 4/2021 | Eddy |
| 2002/0111282 A1 | 8/2002 | Charaf et al. |
| 2002/0170771 A1 | 11/2002 | Milam et al. |
| 2003/0073600 A1 | 4/2003 | Avery et al. |
| 2004/0019286 A1 | 1/2004 | Lia et al. |
| 2004/0151919 A1 | 8/2004 | Bagwell et al. |
| 2004/0166173 A1 | 8/2004 | Albach |
| 2005/0008763 A1 | 1/2005 | Schachter |
| 2005/0035164 A1 | 2/2005 | Badillo |
| 2005/0187580 A1 | 8/2005 | Skiba |
| 2005/0227895 A1 | 10/2005 | Ghosh et al. |
| 2006/0127498 A1 | 6/2006 | Sugiura |
| 2006/0223962 A1 | 10/2006 | Getman et al. |
| 2006/0293623 A1 | 12/2006 | Carroll |
| 2007/0021383 A1 | 1/2007 | Loder |
| 2007/0038132 A1 | 2/2007 | Kishimoto et al. |
| 2007/0038243 A1 | 2/2007 | Rutherford |
| 2007/0042198 A1 | 2/2007 | Schonemyr et al. |
| 2007/0065475 A1 | 3/2007 | Elfersy |
| 2007/0088224 A1 | 4/2007 | Friedman et al. |
| 2007/0129636 A1 | 6/2007 | Friedman et al. |
| 2007/0166344 A1 | 7/2007 | Qu et al. |
| 2007/0193822 A1 | 8/2007 | Statner et al. |
| 2007/0218096 A1 | 9/2007 | Wooley |
| 2007/0227930 A1 | 10/2007 | Bromberg et al. |
| 2007/0275929 A1 | 11/2007 | Fuls et al. |
| 2008/0033329 A1 | 2/2008 | Downs et al. |
| 2008/0166384 A1 | 7/2008 | Jones |
| 2008/0171068 A1 | 7/2008 | Wyner et al. |
| 2008/0193497 A1 | 8/2008 | Samuelsen et al. |
| 2008/0236596 A1 | 10/2008 | Pierskalla et al. |
| 2008/0242794 A1 | 10/2008 | Sandford et al. |
| 2008/0260804 A1 | 10/2008 | Morris et al. |
| 2008/0264445 A1 | 10/2008 | Levitt et al. |
| 2009/0074881 A1 | 3/2009 | Kielbania, Jr. |
| 2009/0196896 A1 | 8/2009 | Patton et al. |
| 2009/0215917 A1 | 8/2009 | Trotter et al. |
| 2009/0223411 A1 | 9/2009 | Higgins et al. |
| 2009/0227454 A1 | 9/2009 | Jaiswal |
| 2009/0252647 A1 | 10/2009 | Orofino |
| 2009/0259157 A1 | 10/2009 | Thomas |
| 2009/0281368 A1 | 11/2009 | Krubsack et al. |
| 2009/0285890 A1 | 11/2009 | Van Den Plas et al. |
| 2009/0288908 A1 | 11/2009 | Giroux et al. |
| 2009/0291147 A1 | 11/2009 | Sandford et al. |
| 2009/0307843 A1 | 12/2009 | Hookway et al. |
| 2009/0312684 A1 | 12/2009 | Leonard et al. |
| 2010/0028462 A1 | 2/2010 | Bolkan et al. |
| 2010/0032231 A1 | 2/2010 | Statner et al. |
| 2010/0056485 A1 | 3/2010 | Park |
| 2010/0063431 A1 | 3/2010 | Bae |

(56) References Cited

U.S. PATENT DOCUMENTS

| | | |
|---|---|---|
| 2010/0086580 A1 | 4/2010 | Nyman et al. |
| 2010/0089408 A1 | 4/2010 | McCaughey et al. |
| 2010/0113871 A1 | 5/2010 | Dias et al. |
| 2010/0137764 A1 | 6/2010 | Eddy |
| 2010/0159256 A1 | 6/2010 | Yamasaki et al. |
| 2010/0167978 A1 | 7/2010 | Iyer et al. |
| 2010/0197748 A1 | 8/2010 | Schwarz et al. |
| 2010/0255178 A1 | 10/2010 | Leander et al. |
| 2010/0331710 A1 | 12/2010 | Eddy |
| 2011/0084578 A1 | 4/2011 | Newkirk et al. |
| 2011/0124772 A1 | 5/2011 | Wang et al. |
| 2011/0186462 A1 | 8/2011 | Storey et al. |
| 2011/0200655 A1 | 8/2011 | Black et al. |
| 2011/0209835 A1 | 9/2011 | Balbona et al. |
| 2011/0233810 A1 | 9/2011 | Neigel et al. |
| 2011/0236504 A1 | 9/2011 | Hata et al. |
| 2011/0245743 A1 | 10/2011 | Eddy |
| 2011/0250626 A1 | 10/2011 | Williams et al. |
| 2011/0271873 A1 | 11/2011 | Ohlhausen et al. |
| 2011/0282302 A1 | 11/2011 | Lopez et al. |
| 2012/0015200 A1 | 1/2012 | Ali et al. |
| 2012/0021405 A1 | 1/2012 | Palzkill et al. |
| 2012/0052106 A1 | 3/2012 | Eddy |
| 2012/0052289 A1 | 3/2012 | Jing et al. |
| 2012/0070481 A1 | 3/2012 | Bolkan et al. |
| 2012/0070509 A1 | 3/2012 | Sugiura |
| 2012/0134953 A1 | 5/2012 | Gentle et al. |
| 2012/0135188 A1 | 5/2012 | Proton |
| 2012/0136313 A1 | 5/2012 | Smith |
| 2012/0157567 A1 | 6/2012 | Ou et al. |
| 2012/0157904 A1 | 6/2012 | Stein |
| 2012/0173274 A1 | 7/2012 | Rensvold et al. |
| 2012/0246788 A1 | 10/2012 | Harrell et al. |
| 2012/0263910 A1 | 10/2012 | Baychar |
| 2012/0296252 A1 | 11/2012 | Cumming et al. |
| 2013/0017242 A1 | 1/2013 | Richardson et al. |
| 2013/0045265 A1 | 2/2013 | Chapman |
| 2013/0101674 A1 | 4/2013 | Toft |
| 2013/0101677 A1 | 4/2013 | Callahan et al. |
| 2013/0231599 A1 | 9/2013 | Eddy |
| 2013/0273132 A1 | 10/2013 | Eddy |
| 2013/0273133 A1 | 10/2013 | Eddy |
| 2013/0338553 A1 | 12/2013 | Eddy |
| 2013/0345170 A1 | 12/2013 | Eddy |
| 2014/0011766 A1 | 1/2014 | Krafft |
| 2014/0051732 A1 | 2/2014 | Ghannoum et al. |
| 2014/0066869 A1 | 3/2014 | Toft |
| 2014/0100504 A1 | 4/2014 | Eddy |
| 2014/0199356 A1 | 7/2014 | Chason et al. |
| 2014/0199358 A1 | 7/2014 | Chason et al. |
| 2014/0199359 A1 | 7/2014 | Chason et al. |
| 2014/0221876 A1 | 8/2014 | Eddy |
| 2014/0256382 A1 | 9/2014 | Eddy |
| 2014/0271794 A1 | 9/2014 | Eddy |
| 2014/0276456 A1 | 9/2014 | Eddy |
| 2014/0302168 A1 | 10/2014 | Perry |
| 2014/0326192 A1 | 11/2014 | Coupe et al. |
| 2014/0352039 A1 | 12/2014 | Abbey et al. |
| 2015/0004361 A1 | 1/2015 | Culpepper |
| 2015/0005684 A1 | 1/2015 | Evans |
| 2015/0011716 A1 | 1/2015 | Lombardi |
| 2015/0024019 A1 | 1/2015 | Ali et al. |
| 2015/0031729 A1 | 1/2015 | Ghannoum et al. |
| 2015/0080827 A1 | 3/2015 | Fogg |
| 2015/0086597 A1 | 3/2015 | Mallak et al. |
| 2015/0089720 A1 | 4/2015 | Abbey et al. |
| 2015/0143615 A1 | 5/2015 | LePage |
| 2015/0158608 A1 | 6/2015 | Talarico |
| 2015/0305343 A1 | 10/2015 | Burke et al. |
| 2015/0328240 A1 | 11/2015 | Hilliard et al. |
| 2015/0352320 A1 | 12/2015 | Eddy |
| 2016/0051389 A1 | 2/2016 | Seligman |
| 2016/0107411 A1 | 4/2016 | Fox et al. |
| 2016/0143275 A1 | 5/2016 | Lan et al. |
| 2016/0143276 A1 | 5/2016 | Lan et al. |
| 2016/0151189 A1 | 6/2016 | Romo et al. |
| 2016/0171179 A1 | 6/2016 | Donofrio et al. |
| 2016/0262382 A1 | 9/2016 | Lan et al. |
| 2016/0262383 A1 | 9/2016 | Lan et al. |
| 2016/0295858 A1 | 10/2016 | Mason et al. |
| 2016/0354005 A1 | 12/2016 | Oakley et al. |
| 2016/0361478 A1 | 12/2016 | Eddy |
| 2017/0000115 A1 | 1/2017 | Nassar et al. |
| 2017/0000651 A1 | 1/2017 | Cumming et al. |
| 2017/0027269 A1 | 2/2017 | Wilson et al. |
| 2017/0081707 A1 | 3/2017 | Dillon et al. |
| 2017/0106622 A1 | 4/2017 | Bonin |
| 2017/0176146 A1 | 6/2017 | Böhringer et al. |
| 2017/0224043 A1 | 8/2017 | Bouchard-Fortin et al. |
| 2017/0236398 A1 | 8/2017 | Eddy et al. |
| 2017/0246041 A1 | 8/2017 | Cumming et al. |
| 2017/0265475 A1 | 9/2017 | Chason et al. |
| 2017/0274114 A1 | 9/2017 | Song et al. |
| 2017/0280716 A1 | 10/2017 | Lan et al. |
| 2017/0319758 A1 | 11/2017 | Eddy et al. |
| 2017/0367899 A1 | 12/2017 | Lundh et al. |
| 2018/0028431 A1 | 2/2018 | Chiattello et al. |
| 2018/0055695 A1 | 3/2018 | Park |
| 2018/0080605 A1 | 3/2018 | Janway et al. |
| 2018/0139959 A1 | 5/2018 | Nassar et al. |
| 2018/0224674 A1 | 8/2018 | Carabin |
| 2018/0243790 A1 | 8/2018 | Grossman et al. |
| 2019/0046081 A1 | 2/2019 | Kilcran et al. |
| 2019/0046082 A1 | 2/2019 | Kilcran et al. |
| 2019/0046083 A1 | 2/2019 | Kilcran et al. |
| 2019/0046084 A1 | 2/2019 | Kilcran et al. |
| 2019/0046364 A1 | 2/2019 | Kilcran et al. |
| 2019/0051137 A1 | 2/2019 | Kilcran et al. |
| 2019/0125774 A1 | 5/2019 | Eddy |
| 2019/0134244 A1 | 5/2019 | Eddy |
| 2019/0166828 A1 | 6/2019 | Storey et al. |
| 2019/0209381 A9 | 7/2019 | Cumming et al. |
| 2019/0216090 A1 | 7/2019 | Alimi et al. |
| 2019/0223445 A1 | 7/2019 | Seo et al. |
| 2019/0254865 A1 | 8/2019 | Eddy |
| 2019/0255210 A1 | 8/2019 | Eddy |
| 2019/0276681 A1 | 9/2019 | Eddy |
| 2019/0289954 A1 | 9/2019 | Baychar |
| 2019/0298479 A1 | 10/2019 | Eddy |
| 2019/0360781 A1 | 11/2019 | Böhringer et al. |
| 2020/0022421 A1 | 1/2020 | Kilbey |
| 2020/0068896 A1 | 3/2020 | Eddy |
| 2020/0071540 A1 | 3/2020 | Eddy |
| 2020/0095775 A1 | 3/2020 | Eddy |
| 2020/0097936 A1 | 3/2020 | Eddy |
| 2020/0281288 A1 | 9/2020 | Eddy |
| 2020/0281774 A1 | 9/2020 | Eddy |
| 2020/0282099 A1 | 9/2020 | Eddy |
| 2021/0052345 A1 | 2/2021 | Eddy |
| 2021/0137120 A1 | 5/2021 | Eddy et al. |
| 2021/0299307 A1 | 9/2021 | Eddy |
| 2021/0299309 A1 | 9/2021 | Eddy |

FOREIGN PATENT DOCUMENTS

| | | |
|---|---|---|
| EP | 1600105 A2 | 11/2005 |
| EP | 2377400 A1 | 10/2011 |
| GB | 2200594 A | 8/1988 |
| KR | 1020060055894 A | 5/2006 |
| RU | 2540478 C1 | 2/2015 |
| RU | 2599004 C1 | 10/2016 |
| WO | 0054587 A1 | 9/2000 |
| WO | 0072850 A1 | 12/2000 |
| WO | 2004087226 A1 | 10/2004 |
| WO | 2005042657 A2 | 5/2005 |
| WO | 2007061625 A2 | 5/2007 |
| WO | 2007076413 A2 | 7/2007 |
| WO | 2008076839 A2 | 6/2008 |
| WO | 2008097599 A2 | 8/2008 |
| WO | 2012037615 A1 | 3/2012 |

(56) References Cited

FOREIGN PATENT DOCUMENTS

| WO | 2013102021 A2 | 7/2013 |
|---|---|---|
| WO | 2016130837 A1 | 8/2016 |

OTHER PUBLICATIONS

Rutala et al., "Guideline for Disinfection and Sterilization in Healthcare Facilities, 2008," Centers for Disease Control (CDC), Department of Health & Human Services, Feb. 15, 2017 (161 pages).

U.S. Food & Drug Administration (FDA), "Reprocessing Medical Devices in Health Care Settings: Validation Methods and Labeling Guidance for Industry and Food and Drug Administration Staff," Mar. 17, 2015 (44 pages).

European Commission, "Aerosol Dispensers Directive Evaluation—Background document", Sep. 23, 2016, Directorate-General for Internal Market, Industry, Entrepreneurship and SMEs, Belgium (1 page).

Monticello, Robert A., "The Use of Reactive Silane Chemistries to Provide Durable, Non-Leaching Antimicrobial Surfaces", AEGIS Environments, Midland, Michigan USA, Jan. 1, 2010 (77 pages).

AEGIS Environments, Material Safety Data Sheet Aegis Microbe Shield(TM) Program—AEGIS(TM) Antimicrobial (Typical Application Strength), Midland, Michigan USA, May 12, 2004 (5 pages).

Federal Institute of Industrial Property, "The International Search Report and the Written Opinion of the International Searching Authority," dated Jan. 24, 2019 (9 pages).

World Health Organization, "Guide to marine sanitation," Third Edition, 2013, pp. 90 and 147-149.

Jimenez et al: "Virucidal activity of a quaternary ammonium compound disinfectant against feline calicivirus: A surrogate for norovirus", AJIC: American Journal of Infection Control, vol. 34, No. 5, Jun. 1, 2006 (Jun. 1, 2006), pp. 269-273, Elsevier, Amsterdam, NL.

Anonymous: "Guidance for the Management of Norovirus Infection in Cruise Ships", • Jul. 1, 2007 (Jul. 1, 2007), pp. 1-76, Retrieved from the Internet: URL:https://virox.com/files docs/content/pdf/msds/1206520183347.pd, [retrieved on Jan. 28, 2021].

Anonymous.: "Guide to ship sanitation (third edition)", Guide to Ship Sanitation (Third Edition), World Health Organization, CH, pp. 1-171, Nov. 30, 2012 (Nov. 30, 2012), Retrieved from the Internet: URL: https://www.who.int/water sanitation health/publications/2011/ship-sanitation-guide/en/, pp. 133-135.

Extended European Search Report, European Application No. 18875379.2, dated Feb. 11, 2021 (6 pages).

Anonymous. 2009. SiSiB PC9911 Antimicrobial. Power Chemical Corp. [online]; downloaded from URL<http://www.powerchemcorp.com/library/public/SiSiB_PC9911.pdf> on Oct. 8, 2013; 2 pages.

http://www.ncbi.nlm.nih.gov/pubmed/7753434, 1995 [retrieved on Dec. 4, 2012].

"Graft Polymerization onto Wool Pretreated with a Mercaptosilane", Textile Research Journal, Aug. 1996, vol. 66, No. 8, 529-532.

Sickbert-Bennett et al., "Comparative Efficacy of Hand Hygiene Agents in the Reductions of Bacteria and Viruses", 2005, pp. 67-77, vol. 33, No. 2, Association for Professionals in Infection Control and Epidemiology, Inc.

http://www.bovie.com/germgate-factsheet1.html [retrieved on Jun. 10, 2010].

http://www.andonline.com/and_med.nsf/html/UA-851THW [retrieved on Jun. 10, 2010].

http://www.zorotools.com/g/Respirator%20Antimicrobial%20Wipes/00118290 [retrieved on Dec. 4, 2012].

ICU Medical, Inc., "MicroClave Neutral Displacement Connector", 2012, M1-1113 Rev. 10, 4 pages.

ICU Medical, Inc., "Antimicrobial MicroClave Neutral Displacement Connector", 2012, M1-1248 Rev. 04, 2 pages.

Anonymous: "Guide to ship sanitation (third edition)", 2011, pp. iii-155 (total pages 171), World Health Organization, Switzerland.

Proguard Quaternary Disinfectant (http://www.kellysolutions.com/wa/showA 1.asp?Basic_EPA_ID=6836%2D78&EPA_ID=6836%2D78%2D1677&Product_Name=Quaternary+Disinfectant+Cleaner+ProGuard (downloaded on Jun. 26, 2013)).

Sarah Coleman, To Bandage or Not To Bandage: Decoding Thoroughbred Leg Wrappings, Dec. 22, 2015, pp. 1-4 https://www.paulickreport.com/horse-care-category/the-great-bandage-debate-decoding-thoroughbred-leg-wrappings/ (Year: 2015).

A-Tape Cohesive Crepe Bandage Red (Pack 2) Elastic Self Adhesive (10 cm x 4.5 mtr) hhttps://www.amazon.in/Bandages-Assorted-Colors-Waterproof-Adherent/dp/B01I62O0CM (Year: 2016).

Measurement Canada document (https://www.ic.gc.ca/eic/site/mc-mc.nsf/vwapj/VCF-FCV_CAS-67-63-0.pdf/$file/NCF-FCV_CAS-67-63-0.pdf, accessed Apr. 15, 2016, pp. 1-2).

Mahltig B., Grethe T., Haase H. (Jun. 1, 2018) Antimicrobial Coatings Obtained by Sol-Gel Method. In: Klein L., Aparicio M., Jitianu A. (eds) Handbook of Sol-Gel Science and Technology. Springer, Cham. ("Antimicrobial").

https://www.fullerindustriesllc.com/franklin-cleaning-technology/quasar/, [retrieved on Nov. 16, 2021].

European Patent Office, "Extended European Search Report", European Application No. 19194187.1, dated Nov. 18, 2019 (12 pages).

http://www.igenericdrugs.com/?s=Life%20Brand%20Disinfectant%20Wipes [retrieved on Dec. 4, 2012].

\* cited by examiner

METHOD OF LIMITING THE SPREAD OF NOROVIRUS WITHIN A CRUISE SHIP

CROSS-REFERENCE TO RELATED APPLICATION

This application is a continuation of and claims priority to U.S. patent application Ser. No. 15/807,157, filed on Nov. 8, 2017, entitled "METHOD OF LIMITING THE SPREAD OF NOROVIRUS WITHIN A CRUISE SHIP," now U.S. Pat. No. 10,967,082, the entire disclosure of which is incorporated herein by reference.

BACKGROUND OF THE INVENTION

The norovirus is a virus that causes gastroenteritis. Gastroenteritis is the inflammation of the gastrointestinal tract, which includes the stomach and the small intestine. Symptoms of gastroenteritis include stomach pain, diarrhea, and vomiting. Norovirus spreads very quickly and easily, including by touching objects that have the norovirus present.

According to the United States Centers for Disease Control and Prevention (CDC), the number of outbreaks of gastroenteritis on cruise ships has increased since 2001, because of increased presence of the norovirus. The CDC even has implemented a Vessel Sanitation Program (VSP) to help cruise ships curtail outbreaks of gastroenteritis. Despite this effort, twelve cruise ships reported an outbreak of gastroenteritis caused by the norovirus in 2015. Eleven cruise ships similarly reported in 2016.

After some outbreaks, the cruise ship may undertake extensive cleaning and disinfecting. The cruise ship owners bear the cost of the cleaning and disinfecting as well as the down time.

SUMMARY OF THE INVENTION

According to an aspect of the present invention, a method of limiting the spread of norovirus within a cruise ship comprises: identifying a surface within a common area of a cruise ship that passengers are likely to touch; and applying a silane quaternary ammonium ion or salt thereof to the surface.

Embodiments of the first aspect of the invention can include any one or a combination of the following features:
the method further comprises identifying the presence of the norovirus within the cruise ship;
the method further comprises wiping the surface with a microfiber cloth;
the method further comprises testing the surface for the presence of the norovirus;
the common area is an elevator and the surface is an elevator button;
the common area is a stairway and the surface is a handrail;
the common area is a casino;
the common area is a dining room;
the common area is a walkway and the surface is a handrail;
the silane quaternary ammonium ion or salt is 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride;
applying a silane quaternary ammonium ion or salt thereof to the surface comprises applying, to the surface, a solution including the silane quaternary ammonium ion or salt thereof and a solvent;
the solvent is isopropyl alcohol;
the solution is applied via spraying the solution onto the surface with an electrostatic sprayer;
the silane quaternary ammonium ion or salt thereof is between 0.1 percent and 10 percent by weight of the solution;
the silane quaternary ammonium ion or salt thereof is between 0.75 percent and 5 percent by weight of the solution;
the silane quaternary ammonium ion or salt thereof is between 1.9 percent and 2.1 percent by weight of the solution;
the solvent is isopropyl alcohol and the isopropyl alcohol is between 30 percent to 90 percent by weight of the solution;
the isopropyl alcohol is between 55 percent and 65 percent by weight of the solution;
the method further comprises initially identifying the presence of the norovirus within the cruise ship, after spraying the solution onto the surface, wiping the surface with a microfiber cloth, and after wiping the surface with a microfiber cloth, waiting a preset period of time, and testing the surface for the presence of the norovirus.

These and other features, advantages, and objects of the present invention will be further understood and appreciated by those skilled in the art by reference to the following specification, claims, and appended drawings.

DETAILED DESCRIPTION

Figure 1:
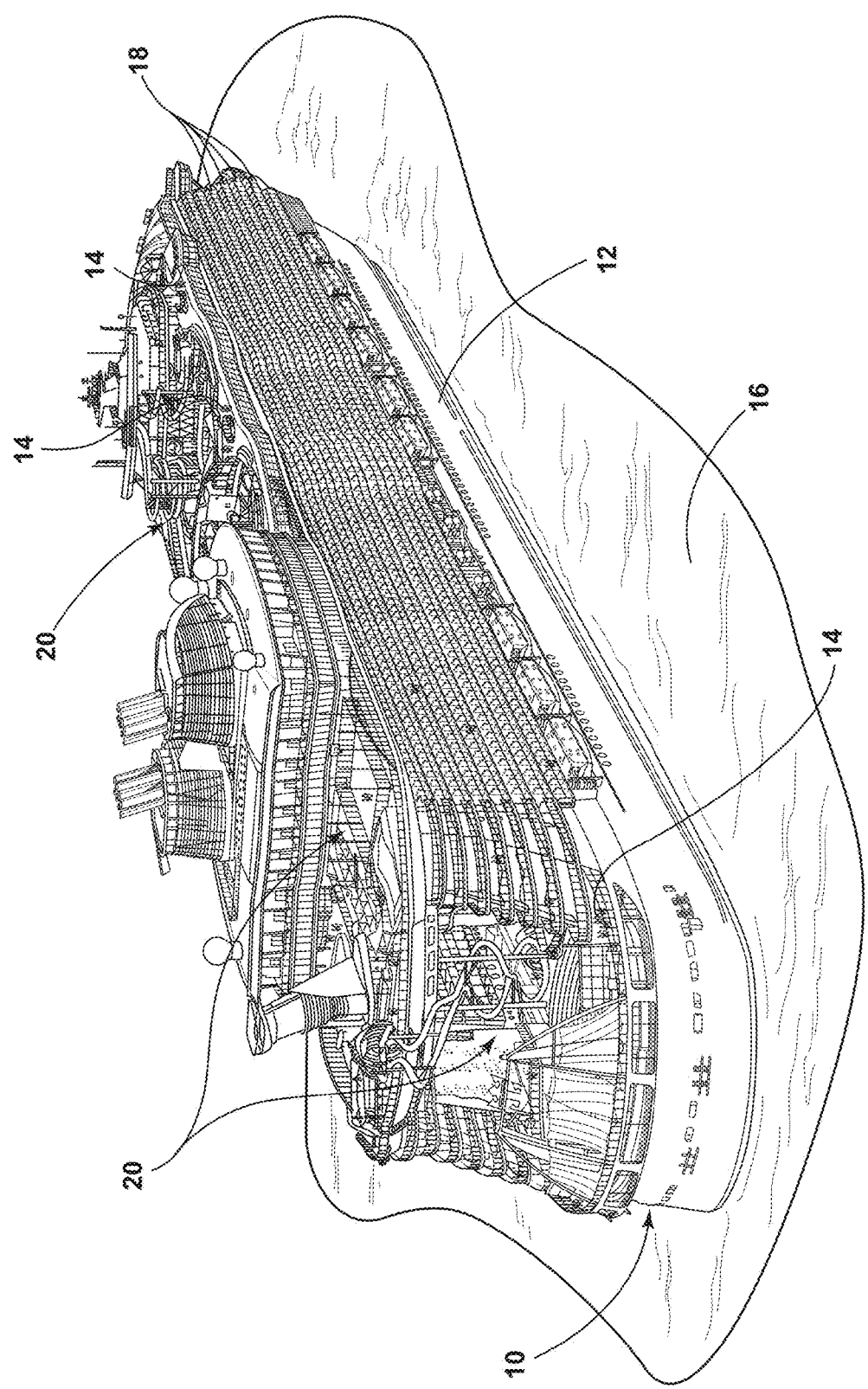
FIG. 1 is a perspective view of a cruise ship, illustrating numerous decks above a hull and passengers being transported over a body of water.
Figure 2:
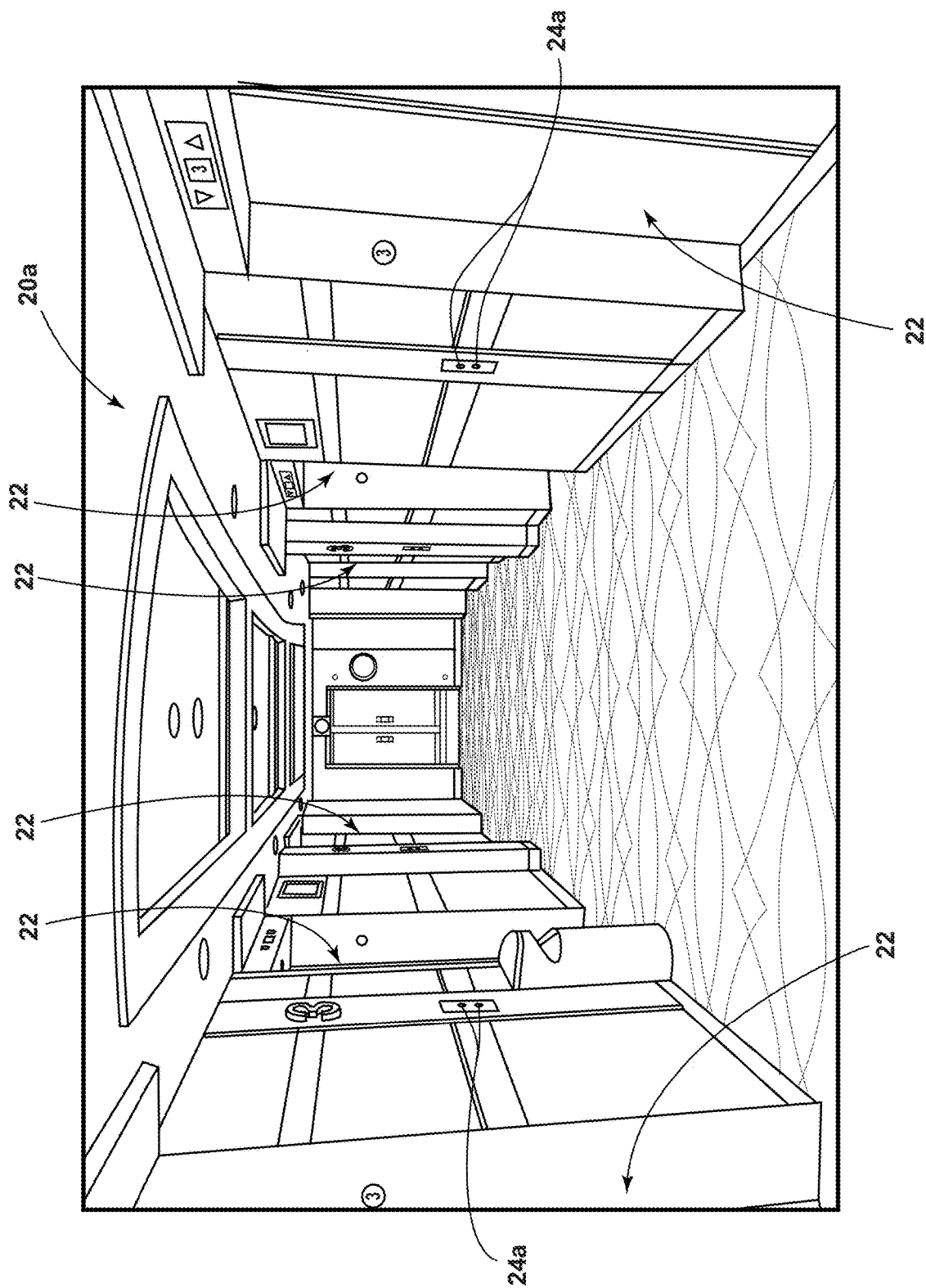
FIG. 2 is a perspective view of an elevator lobby common area and elevator buttons acting as surfaces which passengers are likely to touch.
Figure 3:
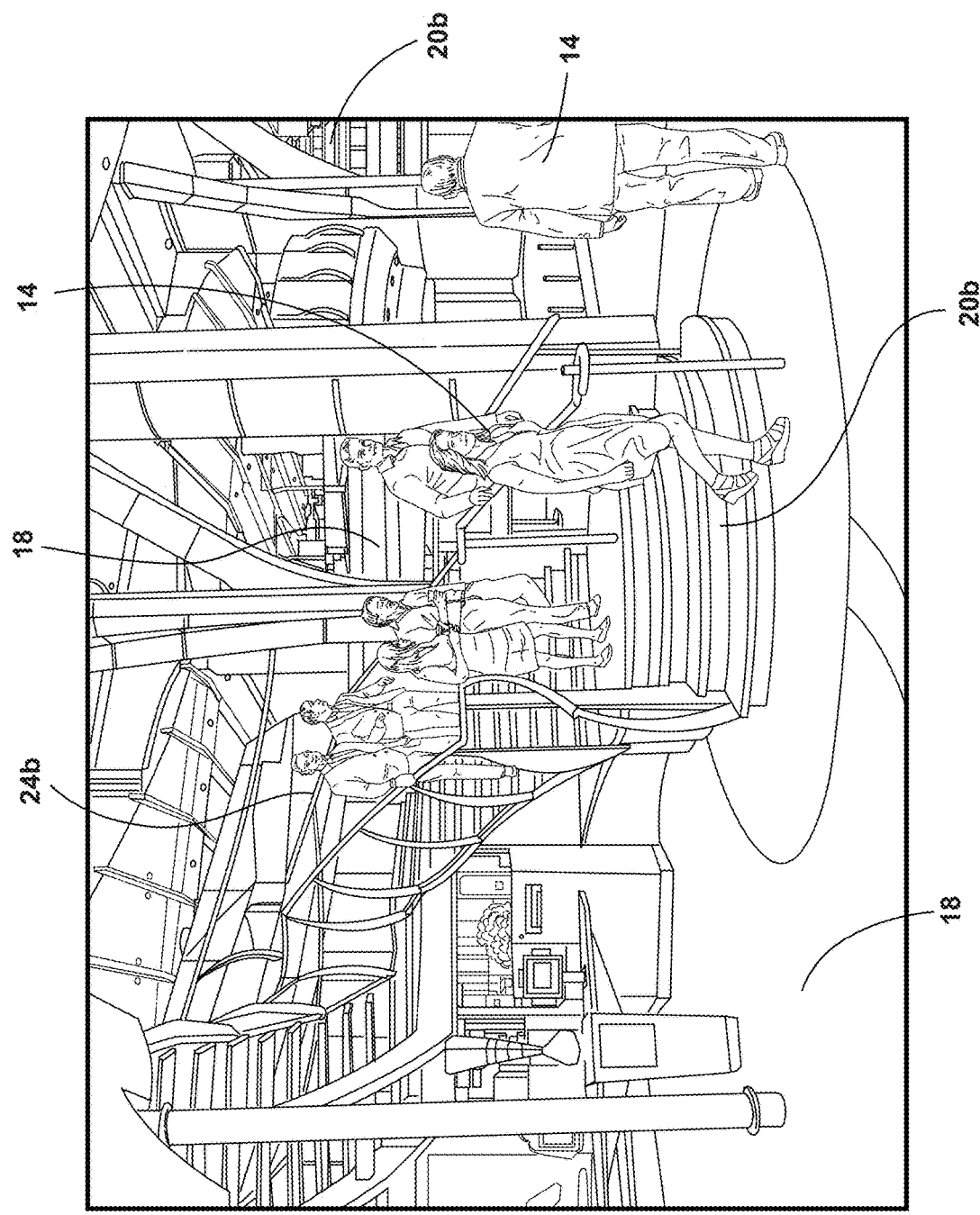
FIG. 3 is a perspective view of several stairways acting as common areas and handrails acting as surfaces which passengers are likely to touch.
Figure 4:
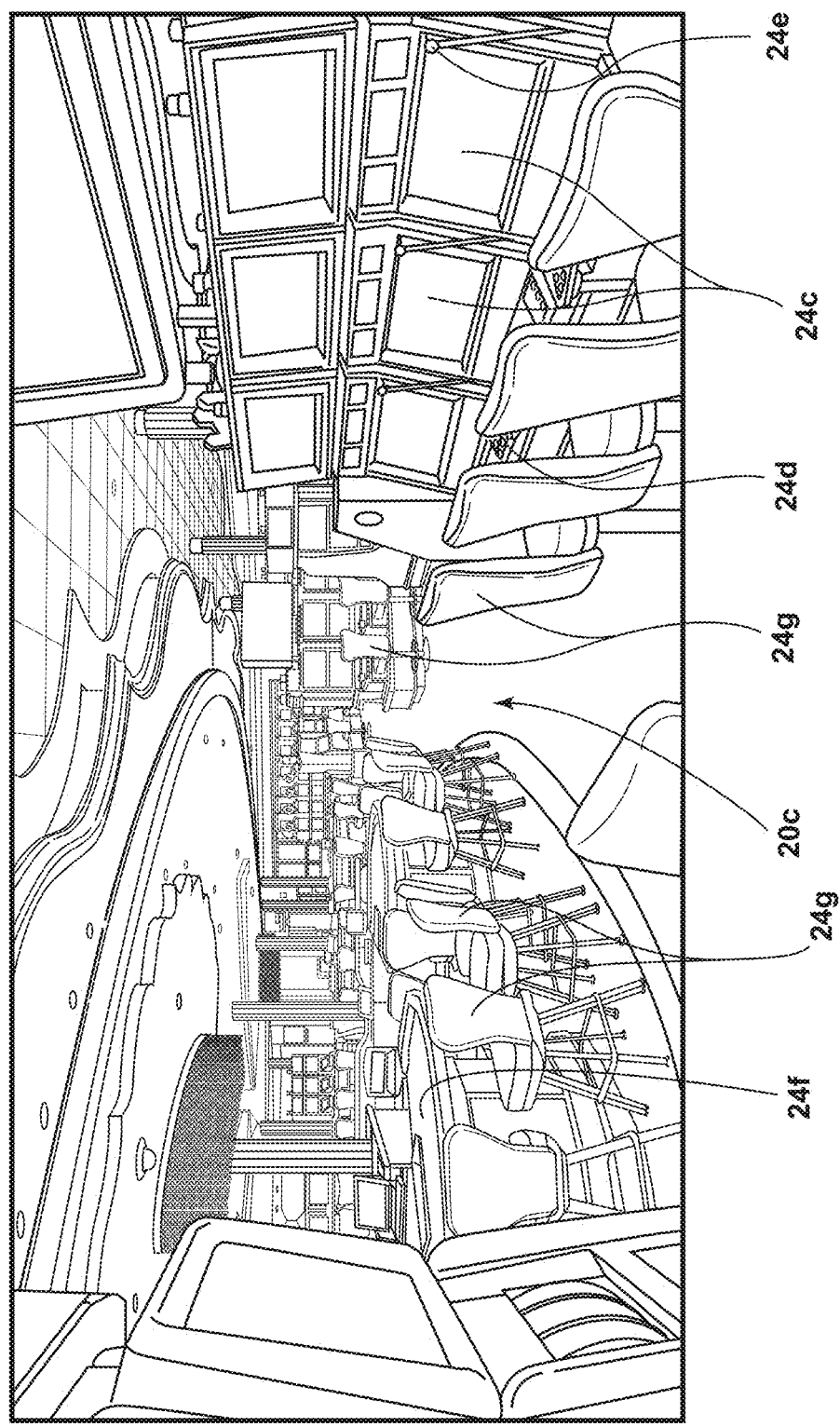
FIG. 4 is a perspective view of a casino acting as a common area for passengers and slot machine buttons acting as surfaces which passengers are likely to touch.
Figure 5:
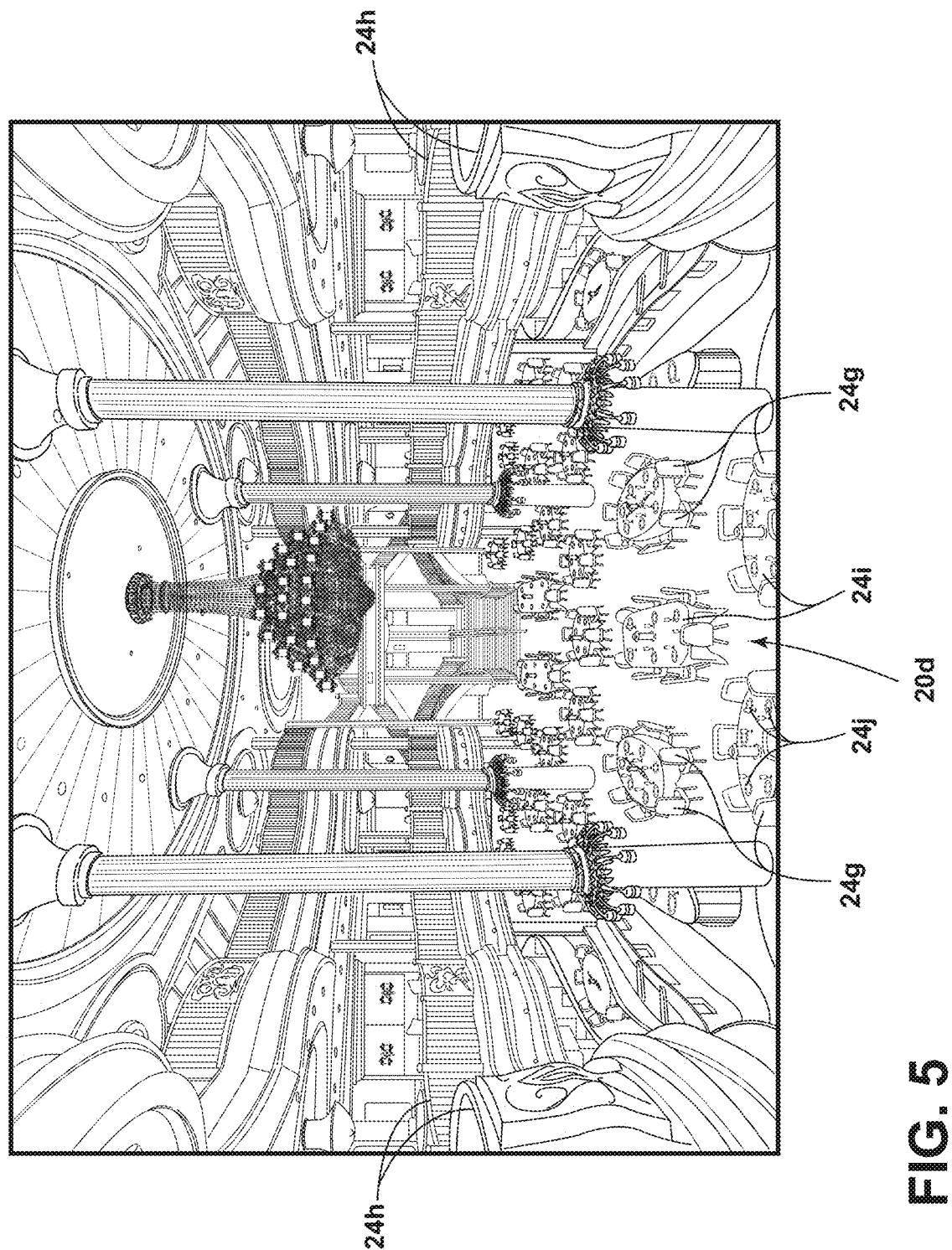
FIG. 5 is a perspective view of a dining room acting as a common area for passengers and dining table tops acting as surfaces which passengers are likely to touch.
Figure 6:
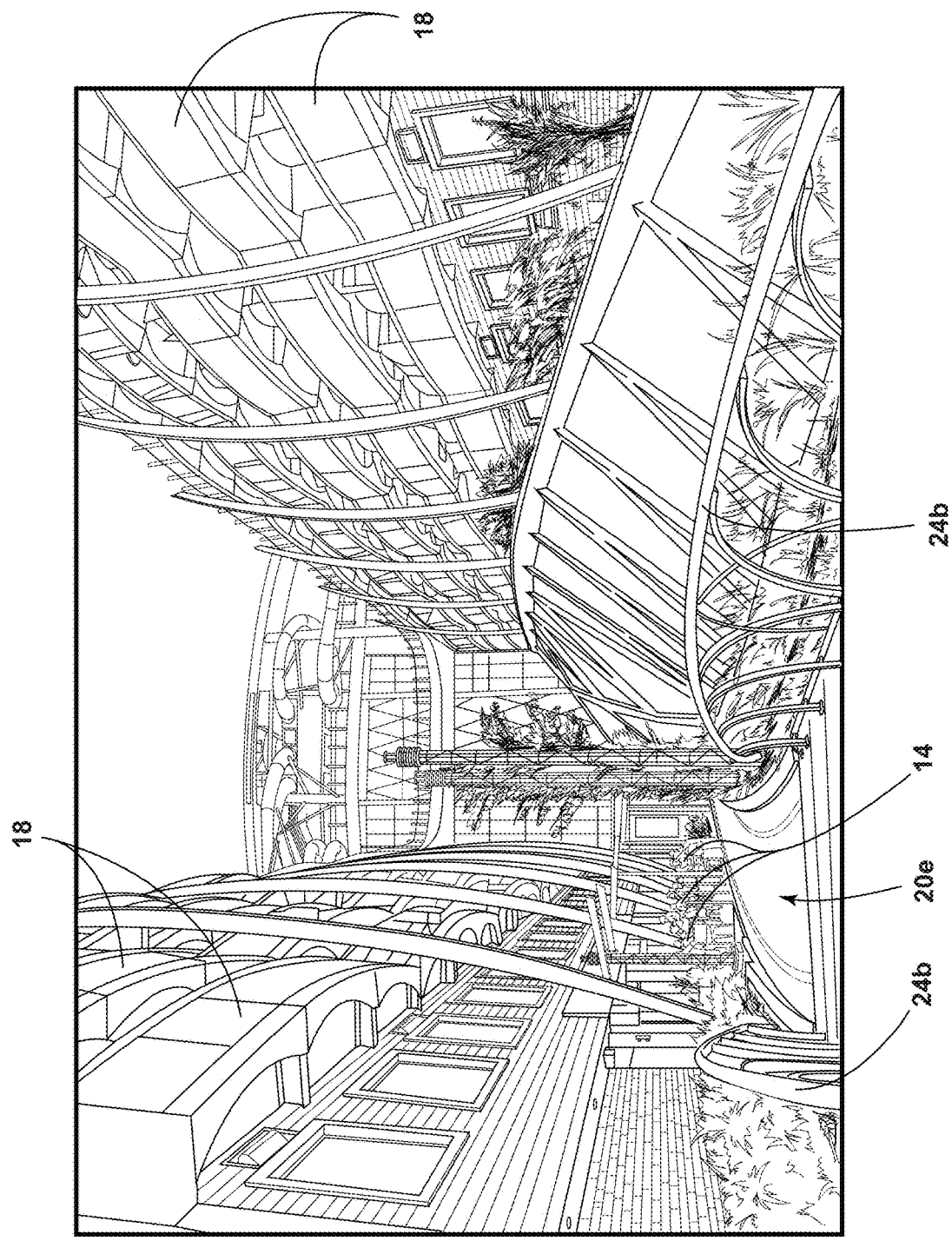
FIG. 6 is a perspective view of a walkway common area and handrails acting as surfaces which passengers are likely to touch.
Figure 7:
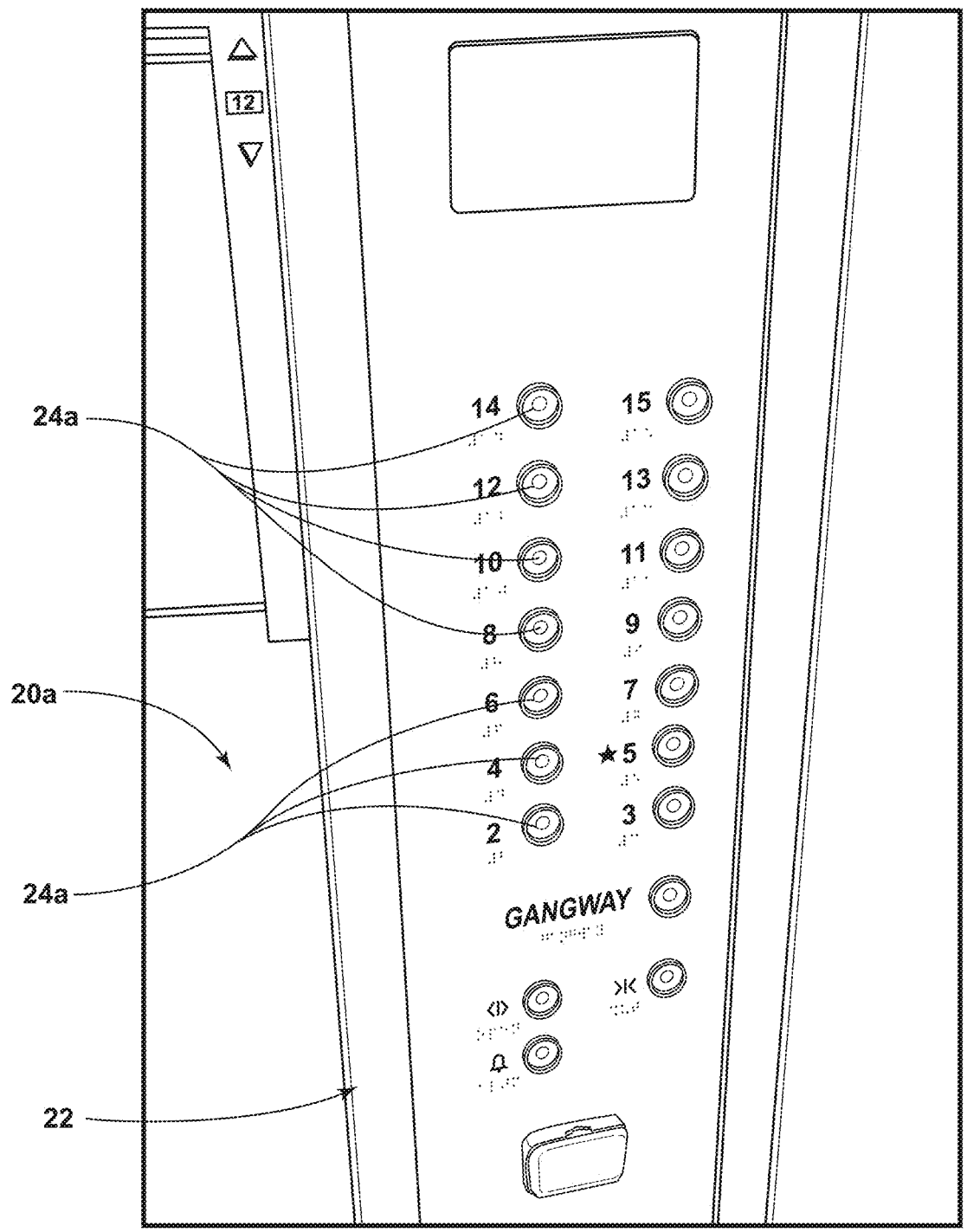
FIG. 7 is a perspective view of elevator buttons within an elevator accessible from the elevator lobby acting as surfaces which passengers are likely to touch.

Referring now to FIGS. 1-7, a cruise ship 10 includes a hull 12 configured to float on, and transport passengers 14 over, a body of water 16. The cruise ship 10 further includes one or more decks 18 within and/or above the hull 12.

The cruise ship 10 further includes one or more common areas 20, which are areas that the passengers 14 are allowed to access, on the one or more decks 18. The common areas 20 include, without limitation, an elevator lobby 20a (see FIG. 2) with elevators 22 transporting passengers 14 between the one or more decks 18, stairways 20b (see FIG. 3) on which passengers 14 can move between the one or more decks 18, a casino 20c (see FIG. 4), a dining room 20d (see FIG. 5), and a walkway 20e upon which passengers 14 walk (see FIG. 6), among other areas. The common areas 20 include surfaces 24 that the passengers 14 are likely to touch with their hands and thus constitute surfaces 24 where the norovirus can transfer from passenger 14 to passenger 14. Examples of such surfaces 24 in the common areas 20 that passengers 14 are likely to touch, include, without limitation: elevator buttons 24a in the elevator lobby 20a (see FIG. 2) and in the elevators 22 (see FIG. 7); handrails 24b for the stairways 20b (see FIG. 3); slot machine screens 24c, buttons 24d, and levers 24e, gaming table tops 24f, and seatbacks 24g in the casino 20c (see FIG. 4); railings 24h, seatbacks 24g, dining table tops 24i, and place settings 24j in the dining room 20d (see FIG. 5); and handrails 24b in the walkway 20e (see FIG. 6).

Figure 8:
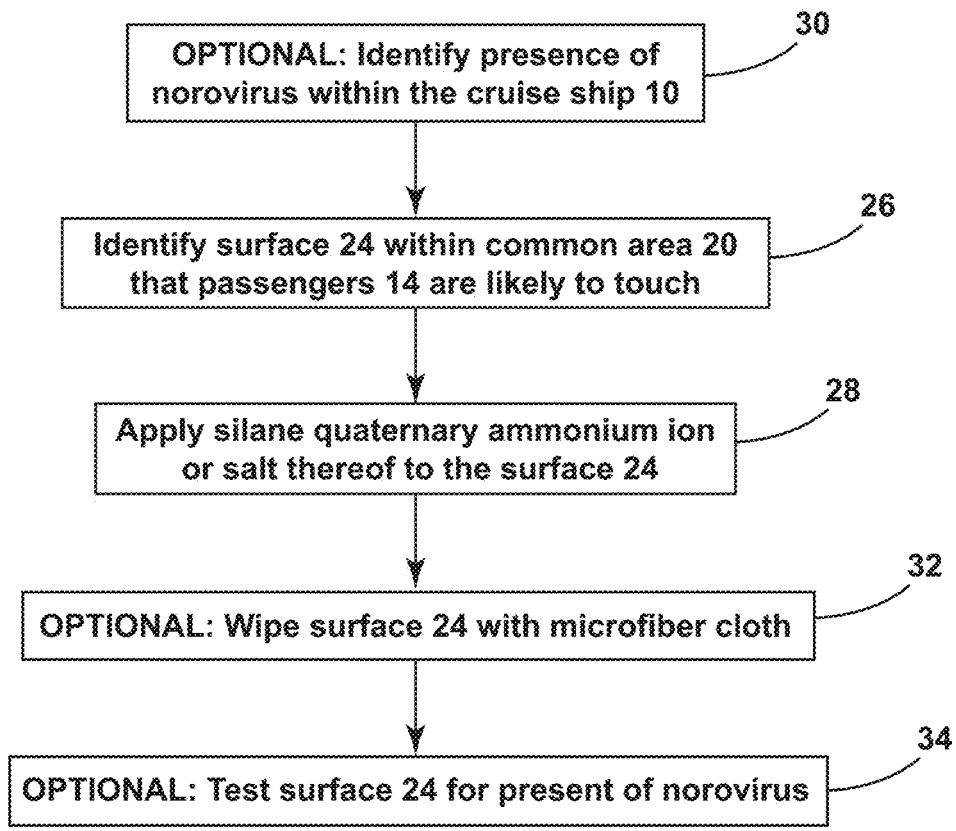
FIG. 8 is a flow chart illustrating a method of limiting the spread of norovirus within a cruise ship, including applying a quaternary ammonium ion or salt thereof to the surface of the common areas which passengers are likely to touch.

Referring now to FIG. 8, at step 26, a method of limiting the spread of norovirus within the cruise ship 10 comprises identifying a surface 24 within a common area 20 of a cruise ship 10 that passengers 14 are likely to touch. Examples of such surfaces 24 in such common areas 20 are provided above. A common area 20 could include any area to which many or all of the passengers 14 have access.

The method further includes, at step 28, applying a silane quaternary ammonium ion or salt thereof to the surfaces 24. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

Applying the silane quaternary ammonium ion or salt thereof to the surface can be made by applying, to the surface 24, a solution including the silane quaternary ammonium ion or salt thereof and a solvent. The solvent can be isopropyl alcohol, among others. The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution. As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

The solution can be applied via spraying the solution containing the silane quaternary ammonium ion or salt thereof and the solvent with an electrostatic sprayer. Alternatively, the solution can be applied with a wipe soaked with the solvent, a spray bottle containing the solvent, and other means.

Quaternary ammonium compounds are generally thought to be ineffective in destroying non-enveloped viruses. The norovirus is a non-enveloped virus. Surprisingly, testing performed pursuant to ASTM E1053 has shown that a solution including 3-(trimethoxysilyl)propyldimethyloctadecyl ammonium chloride as the active ingredient was an effective virucidal solution against a norovirus-like virus. Because of difficulties in propagating norovirus, surrogate viruses which are able to be propagated in cell cultures have been discovered and used for testing purposes. The virus selected for the test was Bacteriophage MS2, which is a virus that infects *Escherichia coli*, and is an accepted surrogate virus for norovirus. Like norovirus, Bacteriophage MS2 is a non-enveloped virus.

For the testing, Petri dish carriers (a sufficient number for both test and control) were presented. The test Petri dish carriers were then sprayed five times with the solution including 3-(trimethoxysilyl)propyldimethyloctadecyl ammonium chloride as the active ingredient. The test Petri dish carriers were sprayed at a distance of between eight and ten inches and at an angle of 45 degrees. The solution was shaken before being sprayed. The test Petri dish carriers with the solution applied thereon were then allowed to dry for fifty-eight minutes. The control Petri dish carriers were not sprayed with the solution including 3-(trimethoxysilyl)propyldimethyloctadecyl ammonium chloride as the active ingredient.

Both the test and control Petri dish carriers were then inoculated with the Bacteriophage MS2 virus. Specifically, the carriers were inoculated with 0.2 ml of the virus, which was spread on the entire surface area on the carrier (10-in$^2$). At time zero, the PFU/Carrier for the control carrier was measured at 9.25E+06. The carriers were then held for twenty-four hours.

Both the test and control carriers were neutralized and the level of the Bacteriophage MS2 virus remaining in each was determined. After the 24 hours holding time, the PFU/Carrier for the control carrier was 1.43E+06, and the PFU/Carrier for the test carrier was 2.95E+04. Thus, the $\log_{10}$ reduction compared to time zero was 0.81 for the control and 2.50 for the test (the carrier sprayed with the solution containing 3-(trimethoxysilyl)propyldimethyloctadecyl ammonium chloride as the active ingredient). The percent reduction compared to time zero was 84.6 percent for the control and 99.7 percent for the test. The $\log_{10}$ reduction for the test compared to the control was 1.68. The percent reduction for the test compared to the control was 97.9 percent. This testing surprisingly demonstrated that the solution containing 3-(trimethoxysilyl)propyldimethyloctadecyl ammonium chloride as the active ingredient satisfied the criteria for passing ASTM E1053, because a greater than 3-$\log_{10}$ reduction was observed in the test carrier compared to the control carrier.

The method can optionally further include, at step 30, identifying the presence of the norovirus within the cruise ship 10. Applying a silane quaternary ammonium ion or salt thereof to the surface 24 set forth above, to limit the spread of the norovirus within a cruise ship 10, can be performed either before the presence of the norovirus has been identified (as a preventative measure) or after the presence of norovirus has been identified (as a consequential measure to limit the spread of the norovirus and to reduce the amount of norovirus within the cruise ship to acceptable levels). The presence of the norovirus can be identified, for example, after an outbreak of sickness on the cruise ship 10. Documenting the existence of gastroenteritis among numerous passengers 14 of the cruise ship 10 can give rise to the assumed identification of the norovirus within the cruise ship 10.

The method can optionally further include, at step 32, wiping the surface 24 with a microfiber cloth. If the solution including the silane quaternary ammonium ion or salt thereof has been applied to the surface 24 via spraying, then beads of the solution may develop on the surface 24. Wiping the surface 24 with a microfiber cloth spreads the solution and therefore the silane quaternary ammonium ion or salt thereof over the surface 24 more uniformly.

The method can optionally further include, at step 34, testing the surface 24 for the presence of the norovirus. After the solution including the silane quaternary ammonium ion or salt thereof has been applied to the surface 24, and after waiting a preset time (such as 24 hours), the surface 24 can be tested for the presence of the norovirus. Such testing can confirm that the silane quaternary ammonium ion or salt thereof applied to the surface 24 has effectively eliminated the norovirus from the surface 24. Alternatively, such testing can confirm whether another application of the silane quaternary ammonium ion or salt thereof to the surface 24 may be required to effectively eliminate the norovirus from the surface 24.

The invention claimed is:

1. A method of limiting spread of a virus within a cruise ship comprising:
   applying, to a surface of a common area of a cruise ship, a solution comprising a silane quaternary ammonium ion or salt thereof and 55 percent and 65 percent by weight isopropyl alcohol;
   wherein, the silane quaternary ammonium ion or salt comprises one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, and 3-(trihydroxysilyl)propyldimethyloctadecyl ammonium chloride.

2. The method of claim 1 further comprising:
   wiping the surface with a microfiber cloth.

3. The method of claim 1 further comprising:
   testing the surface for presence of a virus, after applying the solution, to confirm that the solution has effectively eliminated the virus from the surface.

4. The method of claim 1, wherein the common area is an elevator and the surface is an elevator button.

5. The method of claim 1, wherein the common area is a stairway and the surface is a handrail.

6. The method of claim 1, wherein the common area is a casino.

7. The method of claim 1, wherein the common area is a dining room.

8. The method of claim 1, wherein the common area is a walkway and the surface is a handrail.

9. The method of claim 1, wherein the solution is applied by spraying the solution onto the surface with an electrostatic sprayer.

10. The method of claim 1, wherein the silane quaternary ammonium ion or salt thereof is between 0.1 percent and 10 percent by weight of the solution.

11. The method of claim 1, wherein the silane quaternary ammonium ion or salt thereof is between 0.75 percent and 5 percent by weight of the solution.

12. The method of claim 1, wherein the silane quaternary ammonium ion or salt thereof is between 1.9 percent and 2.1 percent by weight of the solution.

13. The method of claim 1,
   wherein applying the solution comprises:
      applying, via spraying onto the surface with an electrostatic sprayer, the solution, wherein the solution comprises 0.1 percent to 10 percent by weight 3-(trimethoxysilyl)propyldimethyloctadecyl ammonium ion or 3-(trimethoxysilyl)propyldimethyloctadecyl ammonium chloride.

14. The method of claim 13 further comprising:
   before applying the solution, identifying presence of a virus within the cruise ship;
   after spraying the solution onto the surface, wiping the surface with a microfiber cloth; and
   after wiping the surface with the microfiber cloth, waiting a preset period of time, and testing the surface for the presence of the virus;
   wherein, the common area is one of an elevator, a stairway, a casino, a dining room, or a walkway.

15. The method of claim 1, wherein the virus is a norovirus.

16. The method of claim 1 further comprising:
   before applying the solution to the surface, documenting an existence of gastroenteritis among passengers of the cruise ship.

17. The method of claim 16 further comprising:
   identifying the surface as one that passengers are likely to touch and spread a virus.

18. A method of limiting spread of a norovirus within a cruise ship comprising:
   applying, to a surface of a common area of a cruise ship, a solution comprising a silane quaternary ammonium ion or salt thereof and 55 percent and 65 percent by weight isopropyl alcohol;
   wherein, the silane quaternary ammonium ion or salt comprises one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, and 3-(trihydroxysilyl)propyldimethyloctadecyl ammonium chloride.

* * * * *